United States Patent
Liaboe

(10) Patent No.: US 8,663,143 B2
(45) Date of Patent: Mar. 4, 2014

(54) FINGER SUPPORT SYSTEM

(76) Inventor: Philip Liaboe, Reading, MA (US)

(*) Notice: Subject to any disclaimer, the term of this patent is extended or adjusted under 35 U.S.C. 154(b) by 290 days.

(21) Appl. No.: 13/016,676

(22) Filed: Jan. 28, 2011

(65) Prior Publication Data

US 2012/0197169 A1  Aug. 2, 2012

(51) Int. Cl.
*A61F 5/00* (2006.01)
*A61F 5/37* (2006.01)

(52) U.S. Cl.
USPC .............................. 602/22; 128/846

(58) Field of Classification Search
USPC .......... 128/846, 869, 878, 879, 880; 602/1, 5, 602/20–22, 41, 60–62, 64, 23, 30–31; D28/9, 56–57; D24/190–192, 183
See application file for complete search history.

(56) References Cited

U.S. PATENT DOCUMENTS

| | | | | |
|---|---|---|---|---|
| 1,103,465 A | * | 7/1914 | Arrowsmith, Jw | 602/30 |
| 2,416,823 A | * | 3/1947 | Day | 602/30 |
| 3,168,095 A | * | 2/1965 | Magee Richard B | 602/30 |
| 5,282,782 A | * | 2/1994 | Kasahara | 602/30 |
| 7,942,152 B1 | * | 5/2011 | Foster et al. | 128/879 |
| 2003/0230310 A1 | * | 12/2003 | Day | 128/845 |
| 2005/0251081 A1 | * | 11/2005 | McClanahan et al. | 602/30 |
| 2011/0046531 A1 | * | 2/2011 | Lin | 602/30 |

* cited by examiner

*Primary Examiner* — Patricia Bianco
*Assistant Examiner* — Tarla Patel
(74) *Attorney, Agent, or Firm* — Gary L. Huusko

(57) ABSTRACT

A finger support system comprising a wedge shaped finger support member, narrow at one end and wider at another end, with concave sides to form fit the finger support member between an injured and an adjacent finger, the finger support member being taped or otherwise removable attached between the injured and adjacent fingers with the narrow end fitting snugly at the juncture of the two fingers and the wider end separating the fingers, and extending past the middle knuckle but not to the knuckle near the finger tips so that, when the finger support member is taped in place, the hand will have greater use in basketball or other ball-handling sports.

2 Claims, 3 Drawing Sheets

FINGER SUPPORT SYSTEM

BACKGROUND OF THE INVENTION

1. Field of the Invention

Figure 1:
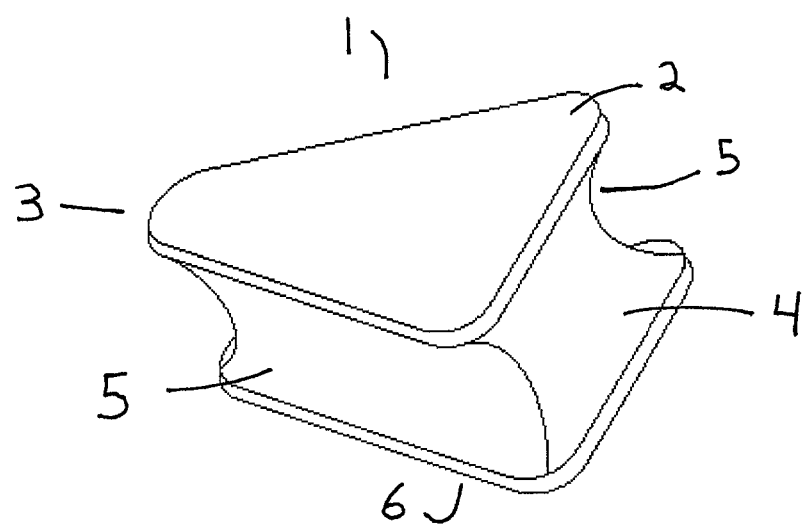

The present invention is related to an apparatus for supporting fingers that have been injured. More particularly, the present invention is directed to a finger support system that stabilizes the injured finger or fingers while allowing the fingers to maintain a spread, normal healthy position.

2. Description of Related Art

Hand and finger injuries in various sports are very prevalent and occur with frequency for many participants. Depending on the seriousness of the injured finger and the pain threshold of the player, many times the player can continue participation in the sport with some type of support for the injured finger. Often times, treatment requires that the affected finger or fingers be immobilized with a splint or taped to an adjacent, uninjured finger.

Prior art splints include straight flat wooden or metal sticks or curved metal designed to fit more closely to the finger that are bound to the injured fingers. These types of splints do not allow a finger to be positioned in any particular manner other than merely holding the finger straight.

In many cases, the suggested method for providing support in the case of the jammed or sprained finger is to tape the injured finger to one of the adjoining fingers. In some circles, this is referred to as "buddy taping" the finger where the injured finger is "buddy taped" to a healthy finger that is next to it. Buddy taped fingers allow the injured finger to be supported by the healthy finger to reduce pain when playing and prevent re-injury. Fingers that have been jammed or sprained are weaker and more susceptible to re-injury during play. Buddy taping allows the player to continue to play with the injured finger with less pain, more confidence and a reduced chance of further injury. The disadvantage to buddy taping is that fingers that are taped together are no longer able to spread apart to the normal, healthy position.

For playing sports, particularly at a high level like high school varsity, college or professional levels, this can be a significant change in the shape of the hand, thus handicapping the player to a certain degree. The player can still play the sport with the buddy taped finger; however, may not have the peak performance they are accustomed to. The reason is that the shape of the hand and position of the fingers has changed from the position that they have been accustomed to playing and practicing their sport. Buddy taping the pinky finger to the ring finger reduces the shape of the hand with the fingers spread by as much as 16%. The solution is to provide the same or better support for the injured finger while enabling the fingers and the hand to function in its normal "fingers spread" position.

SUMMARY OF INVENTION

Accordingly, it is a primary object of the present invention to provide a finger support system for two or more adjacent fingers that easily allows the fingers to maintain a more normal spread position thereby allowing a fuller and normal use of the hand during sports activities, particularly basketball or other similar activities. The invention is a finger support system comprising a finger support member with a somewhat wedge shape for placement between an injured finger and an adjacent finger, the support member being removably attachable to the injured and adjacent fingers, thereby providing support of the injured finger while allowing use of the hand with the injured finger.

SUMMARY DESCRIPTION OF DRAWINGS

Figure 2:
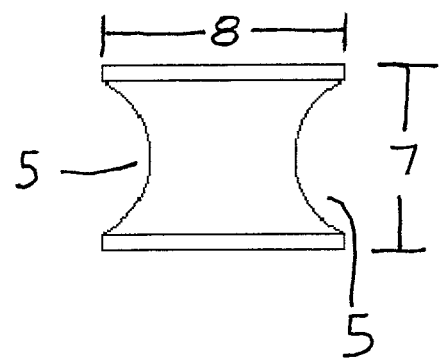
Figure 3:
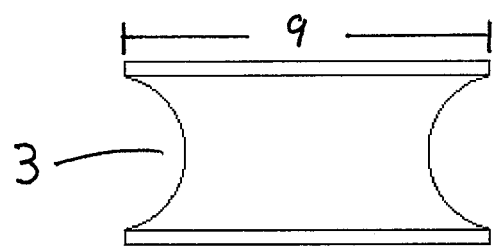
Figure 4:
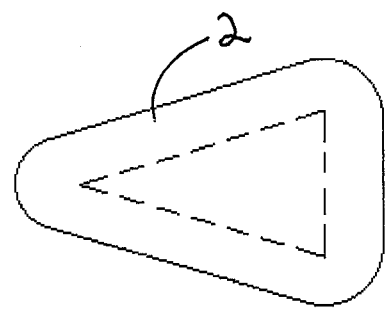

FIG. 1 is a perspective view of the finger support.
FIG. 2 is an end view of the finger support.
FIG. 3 is a side view of the finger support.
FIG. 4 is a top view of the finger support.

DETAILED DESCRIPTION OF DRAWINGS

Referring to FIG. 1, the finger support 1 is shown with a top surface 2, a narrow end 3, a wider end 4, two sides 5 and a bottom surface 6, the top surface and bottom surface being triangular shaped and planar. As will be described below, the top and bottom surfaces may have a curvature, rather than a planar surface.

Referring to FIG. 2, the concave surface of each side is shown. The preferred embodiment shows the top surface and bottom surface defining a height 7 there between. The height is sufficient enough to provide the needed support but not greater than the thickness of a typical finger.

Referring again to FIG. 1, the finger support is generally a wedge shape, thus defining the narrow end and the wider end with a length extending from the narrow end to the wider end, the wider end also comprising a width.

Referring to FIGS. 2 and 3, the width 8 of the wider end is sufficient to provide adequate spread between the fingers and the length 9 is sufficient to provide support past the middle knuckle but does not extend to the knuckle near the finger tip thereby giving the player full use of the finger tips after securing the finger support. The two sides 5 each comprise a concave surface generally to form fit the injured finger and adjacent finger to the finger support in a comfortable and snug fashion. The narrow end 3 comprises a concave surface generally to form fit the finger support to the hand at the juncture where the injured finger and adjacent finger meet. The concave surfaces could also be beveled or grooved to allow for both fingers to rest inside and at the bottom for a snug and comfortable fit.

Referring to FIG. 3, the concave surface of the narrow end 3 is shown. The wider end can also have a concave surface, however, the existence of that wider end concave surface would be for ease of manufacture, and has no real benefit or detriment for the finger support.

Referring now to FIG. 4, the top 2 is shown with dashed lines indicating the depth of each concave surface of the sides and the ends.

The finger support is made out of a firm, yet soft material. A preferred embodiment would have the finger support made of closed cell polyurethane, however, many other types of lightweight cellular foam or like materials that are firm, soft and comfortable and somewhat pliable, and yet supportive, could be used as well.

In use, the finger support would be placed between an injured finger and an adjacent finger with the narrow end towards the hand such that the fingers would be positioned apart, widening towards the wider end of the finger support. The injured finger and adjacent finger would fit snugly in the concave recess of the finger support sides, and the finger support would be taped or otherwise secured to the fingers so that the fingers would be held securely to the finger support, thereby allowing the adjacent finger to provide support to the injured finger. The finger support would extend just beyond the middle knuckle of each finger, allowing the finger tips movement at the knuckle adjacent to the finger tips. The finger support, when properly used, would allow the fingers to be more normally spaced apart, thereby allowing the person to be able to use the hand more effectively and safely in a sports activity, such as basketball or the like.

A preferred embodiment of the finger support would have the wider end width being between 1 and 1½ inches, the length being between 1½ and 1¾ inches, the radius of the concave surfaces being between 5/16 and 11/32 inches, and the height being ¾ of an inch. The length would be sufficiently long to extend the finger support member beyond the middle knuckles of the injured and adjacent fingers, but not so long as to extend to the knuckle near the finger tip of each finger. This will allow the finger tips of the injured and adjacent fingers to move, thus providing greater use of the hand, especially in basketball or like sports. The dimensions disclosed herein are not limitations nor are they proportional and depending upon the size of the hand of the person with an injured finger, the finger support may be larger or smaller and each dimension may vary, even disproportionately to the other disclosed dimensions.

The finger support could also be a slightly curved shape from wider end to the narrow end to conform to the shape the hand would take when handling a basketball or football. The curved embodiment would have the bottom planar surface to instead have a somewhat concave curvature along the length of the finger support and the top planar surface to instead have a somewhat convex curvature along the length of the finger support.

I claim:

1. A support system for an injured finger of a hand, receiving support from an adjacent finger comprising a wedge shaped finger support member made of a lightweight cellular foam material, with a top surface, a bottom surface, a narrow end, a wider end, two sides, a length extending from the narrow end to the wider end, the length having a dimension of between 1½ inches and 1¾ inches, and an attachment means to attach the finger support member to the injured finger and adjacent finger, the top surface and bottom surface each being planar and defining a height there between of ¾ of an inch, the wider end comprising a width of between 1 inch and 1½ inches, the two sides each comprise a concave surface generally to form fit the injured finger and adjacent finger to the finger support member, the narrow end comprising a concave surface generally to form fit the finger support member to the hand where the injured finger and adjacent finger meet wherein the concave surface of each side and of the narrow end has a radius between 5/16 of an inch and 11/32 of an inch.

2. A finger support system for an injured finger receiving support from an adjacent finger comprising a wedge shaped finger support member made of closed cell polyurethane with a top surface, a bottom surface, a narrow end, a wider end, two sides, a length of between 1½ inches and 1¾ inches extending from the narrow end to the wider end, and an attachment means to attach the finger support member to the injured finger and adjacent finger, the top surface and bottom surface each being planar and defining a height there between of ¾ of an inch, the wider end comprising a width of between 1 inch and 1½ inches, the two sides each comprise a concave surface with a radius of between 5/16 of an inch and 11/32 of an inch generally to form fit the injured finger and adjacent finger to the finger support member, the narrow end comprising a concave surface with a radius of between 5/16 of an inch and 11/32 of an inch generally to form fit the finger support member to the hand where the injured finger and adjacent finger meet, whereby the finger support member is taped or otherwise removably attached to the injured and the adjacent finger such that the narrow end fits snugly to the juncture where the injured and adjacent fingers meet, the sides fit snugly to each respective finger, and the linger support member extends past the middle knuckles of each finger but not to the knuckle nearest the finger tip, thereby providing support for the injured finger yet allowing greater use of the hand and finger tips.

* * * * *